United States Patent
Wen et al.

(10) Patent No.: US 11,536,421 B1
(45) Date of Patent: Dec. 27, 2022

(54) MULTIFUNCTIONAL LIGHT SOURCE ASSEMBLY AND MULTIFUNCTIONAL DESK LAMP APPLYING SAME

(71) Applicants: Shanghai Sansi Electronic Engineering Co. Ltd., Shanghai (CN); Shanghai Sansi Technology Co. Ltd., Shanghai (CN); Jiashan Sansi Optoelectronic Technology Co. Ltd., Jiaxing (CN); Pujiang Sansi Optoelectronic Technology Co. Ltd., Jinhua (CN)

(72) Inventors: Xing Wen, Shanghai (CN); Xiaoliang He, Shanghai (CN); Guoli Zhu, Shanghai (CN); Congyi Lin, Shanghai (CN)

(73) Assignees: Shanghai Sansi Electronic Engineering Co. Ltd., Shanghai (CN); Shanghai Sansi Technology Co. Ltd., Shanghai (CN); Jiashan Sansi Optoelectronic Technology Co. Ltd., Zhejiang (CN); Pujiang Sansi Optoelectronic Technology Co. Ltd., Zhejiang (CN)

( * ) Notice: Subject to any disclaimer, the term of this patent is extended or adjusted under 35 U.S.C. 154(b) by 0 days.

(21) Appl. No.: 17/560,282

(22) Filed: Dec. 23, 2021

(30) Foreign Application Priority Data

Jul. 5, 2021 (CN) .......................... 202121514784.1

(51) Int. Cl.
*F21S 6/00* (2006.01)
*F21V 23/00* (2015.01)
(Continued)

(52) U.S. Cl.
CPC .............. *F21S 6/003* (2013.01); *A01G 7/045* (2013.01); *A61L 2/10* (2013.01); *F21V 5/045* (2013.01);
(Continued)

(58) Field of Classification Search
CPC ......... F21S 6/003; A61L 2/10; A61L 2202/11; A01G 7/045; F21V 29/50; F21V 5/045; F21V 21/26; F21V 23/003; F21V 23/0485
See application file for complete search history.

(56) References Cited

U.S. PATENT DOCUMENTS

| 6,921,182 B2 * | 7/2005 | Anderson, Jr. ........ A01G 7/045 362/800 |
| 8,092,065 B2 * | 1/2012 | Yeh ...................... G02B 6/0068 362/613 |

(Continued)

*Primary Examiner* — Arman B Fallahkhair

(57) ABSTRACT

A multifunctional light source assembly and a multifunctional desk lamp are disclosed. The multifunctional desk lamp includes a base assembly, a lamp head assembly, and a lamp arm assembly; one end of the lamp arm assembly is connected with the base assembly, and the other end is connected with and supports the lamp head assembly; the lamp head assembly is internally provided with the multifunctional light source assembly, the multifunctional light source assembly includes an illumination LED chip, a plant grow light LED chip and an ultraviolet LED chip. The illumination chip, the plant grow light chip and the ultraviolet chip are respectively connected to a controller, which respectively controls the three chips, through the on and off of currents, so that functions such as illumination for reading and writing, sterilization, plant growth assistance can be achieved.

4 Claims, 2 Drawing Sheets

(51) Int. Cl.
*F21V 21/26* (2006.01)
*F21V 29/50* (2015.01)
*F21V 5/04* (2006.01)
*A01G 7/04* (2006.01)
*A61L 2/10* (2006.01)
*F21V 23/04* (2006.01)
*F21Y 115/10* (2016.01)
*F21Y 113/10* (2016.01)

(52) U.S. Cl.
CPC ............ *F21V 21/26* (2013.01); *F21V 23/003* (2013.01); *F21V 23/0485* (2013.01); *F21V 29/50* (2015.01); *A61L 2202/11* (2013.01); *F21Y 2113/10* (2016.08); *F21Y 2115/10* (2016.08)

(56) References Cited

U.S. PATENT DOCUMENTS

| | | | | |
|---|---|---|---|---|
| 8,100,552 | B2 * | 1/2012 | Spero | H05B 45/395 362/276 |
| 8,299,445 | B2 * | 10/2012 | Yamada | A01G 9/249 250/455.11 |
| 11,166,415 | B2 * | 11/2021 | Barber, III | A61L 2/0076 |
| 11,318,220 | B1 * | 5/2022 | Patterson | A61L 2/24 |

* cited by examiner

MULTIFUNCTIONAL LIGHT SOURCE ASSEMBLY AND MULTIFUNCTIONAL DESK LAMP APPLYING SAME

CROSS REFERENCE TO RELATED APPLICATION

The present application claims the benefit of priority to Chinese Patent Application No. CN 2021215147841, entitled "MULTIFUNCTIONAL LIGHT SOURCE ASSEMBLY AND MULTIFUNCTIONAL DESK LAMP APPLYING SAME", filed with CNIPA on Jul. 5, 2021, the disclosure of which is incorporated herein by reference in its entirety for all purposes.

FIELD OF TECHNOLOGY

The present disclosure relates to technical field of multifunctional lamps, in particular to a multifunctional light source assembly and a multifunctional desk lamp applying the same.

BACKGROUND

Lamps are no longer only for lighting purposes. Various multifunctional desk lamps or bedside lamps have emerged on the market in order to meet people's individualized needs. Meanwhile, the global epidemic has also made people focus more on health and hygiene, and as a result, numerous lamps with a sterilization function are popping up on the market.

However, desk lamps on the market still cannot offer every function that people need in everyday life.

SUMMARY

The present disclosure provides a multifunctional light-emitting device, including: a multifunctional light source assembly, which includes an illumination LED chip, a plant grow light LED chip and an ultraviolet LED chip; wherein the multifunctional light source assembly is controlled to perform one or more functions of illumination, plant growth assistance and sterilization.

In some embodiments of the present disclosure, the multifunctional light-emitting device further includes a control part; wherein the control part correspondingly controls the light source assembly when responding to a user operation, such that the light source assembly performs one or more functions of illumination, plant growth assistance and sterilization.

In some embodiments of the present disclosure, the multifunctional light-emitting device further includes a communication part, wherein the communication part establishes a communication connection with an external control device, to correspondingly control the light source assembly to perform one or more functions of illumination, plant growth assistance and sterilization after receiving light control instructions from the external device.

The present disclosure further provides a multifunctional desk lamp, including: a base assembly; a lamp head assembly; and a lamp arm assembly, wherein one end of the lamp arm assembly is connected with the base assembly, and the other end is connected with and supports the lamp head assembly; wherein the lamp head assembly is internally provided with a multifunctional light source assembly, the multifunctional light source assembly includes an illumination LED chip, a plant grow light LED chip and an ultraviolet LED chip; and the light source assembly is controlled to perform one or more functions of illumination, plant growth assistance and sterilization.

In some embodiments of the present disclosure, the lamp arm assembly includes: a vertical arm, wherein a first end of the vertical arm is connected with the base assembly; a horizontal arm, wherein a first end of the horizontal arm is connected with a second end of the vertical arm through a first rotating part, and a second end of the horizontal arm is connected with the lamp head assembly through a second rotating part; wherein the first rotating part rotates and drives the horizontal arm and the lamp head assembly to rotate around the vertical arm; and the second rotating part rotates and drives the lamp head assembly to rotate around the horizontal arm.

In some embodiments of the present disclosure, the lamp head assembly includes: a lamp cover, including an accommodating space; a heat dissipation part, arranged in the accommodating space configured for accommodating the light source assembly; a cover plate, covering the lamp cover; and a lens, arranged on the cover plate.

In some embodiments of the present disclosure, the cover plate includes three light-transmitting areas corresponding to the illumination LED chip, the plant grow light LED chip and the ultraviolet LED chip, respectively.

In some embodiments of the present disclosure, the lens arranged on the cover plate is a Fresnel lens; the three light-transmitting areas of the cover plate include a hollow part for transmission of ultraviolet light, a bright surface lens for transmission of plant grow light, and the Fresnel lens for transmission of the light for illumination.

In some embodiments of the present disclosure, the heat dissipation part includes a ceramic radiator and an aluminum radiator; one side of the ceramic radiator is for attaching to the light source assembly and the other side is connected with the aluminum radiator.

In some embodiments of the present disclosure, the base assembly includes a drive power module and a touch panel; when the touch panel is touched, it transmits corresponding lamp control instructions to the drive power module through an interface; the drive power module is configured to have three light control circuits, and each light control circuit is configured to independently drive different LED chips.

As mentioned above, the multifunctional light source assembly and the multifunctional desk lamp applying the same of the present disclosure have the following beneficial effects: the desk lamp is provided with an illumination LED chip, a plant grow light LED chip and an ultraviolet LED chip, which are respectively connected to the touch pad, so that independent control of the three chips is realized, through the on and off of currents, functions such as illumination for reading, ultraviolet sterilization and plant growth assistance are achieved. In addition, when the ultraviolet sterilization function is activated, the illumination function can also be activated so that it will more safe for the user to use the ultraviolet sterilization function; compared to traditional methods for heat dissipation, the heat dissipation method herein that adopts both aluminum and ceramic materials is more efficient, and has a better insulation effect and corrosion-resistance property, thereby improving the overall performance of the lamp.

DETAILED DESCRIPTION

Figure 1:
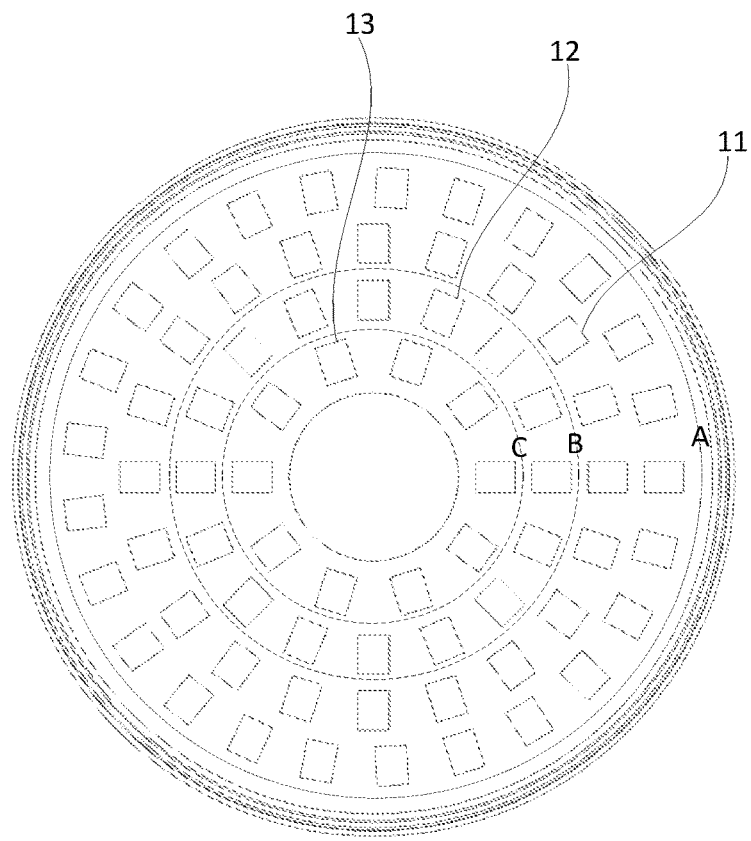
FIG. 1 shows a structural diagram of a multifunctional light-emitting device according to an embodiment of the present disclosure.

The following embodiments illustrate implementations of the present disclosure, and those familiar with the art can readily understand other advantages and benefits of the present disclosure from the contents disclosed in the present specification.

It should be noted that the structure, proportion, size and the like shown in the drawings attached to the present specification are merely used to illustrate the contents disclosed in the specification for those familiar with the technology to understand and read, and are not used to limit the conditions under which the present disclosure can be implemented. Any modification of the structure, change of the proportional relationship or adjustment of the size, without affecting the efficacy and the objective of the present disclosure, should still fall within the scope of the contents disclosed in the present disclosure. The following detailed description should not be considered as limiting. The terms used herein are intended to describe particular embodiments only and are not intended to limit the present application. Spatially terms such as "up", "down", "left", "right", "below", "under", "lower part", "above", "upper part" and the like may be used in the text to illustrate the relationship of one element or feature shown in the drawing to another element or feature.

In the present disclosure, unless otherwise stipulated and defined definitely, such terms as "installed", "connected", "in connection", "fixed" and "fixedly clamped" should be understood in their broad sense, e.g., the connection can be a fixed connection, a detachable connection or an integral connection; can be mechanical connection or electrical connection; can be direct connection or can be indirect connection through an intermediate, and can also be communication between two elements. For those skilled in the art, the specific meanings of the above terms in the present disclosure can be understood according to specific conditions.

Further, as used herein, singular nouns using "one", "a" and "the" are also intended to include the plural forms, unless the context indicates otherwise. It should be further understood that the terms "comprise", "include" indicate the presence of the feature, operation, component, assembly, item, type, and/or group, but do not exclude the presence, occurrence, or addition of one or more other features, operations, components, assemblies, items, types, and/or groups. The terms "or" and "and/or" as used herein are construed to be inclusive or to imply any one or any combination. Therefore, "A, B or C" or "A, B and/or C" means any of the following: A; B; C; A and B; A and C; B and C; A, B, and C. Exceptions to this definition occur only when combinations of components, functions, or operations are inherently mutually exclusive in some way.

The present disclosure provides a multifunctional desk lamp which integrates multiple functions such as indoor illumination, plant growth assistance and ultraviolet sterilization into one lamp, thereby saving space; when the ultraviolet sterilization function is activated, the illumination function can also be activated so that it will be safer for the user to use the ultraviolet sterilization function; compared with traditional methods for heat dissipation, the heat dissipation method herein that adopts both aluminum and ceramic materials is more efficient, and has a better insulation effect and corrosion-resistance property, thereby improving the overall performance of the lamp.

The technical solutions of the present disclosure are described in further details by the following embodiments and in combination with the accompanying drawings. It should be understood that the specific embodiments described herein are intended to explain the present disclosure only and are not intended to limit the present disclosure.

FIG. 1 shows a structural diagram of a multifunctional light-emitting device according to an embodiment of the present disclosure. The multifunctional light-emitting device includes a multifunctional light source assembly; the multifunctional light source assembly includes an illumination LED chip 11, a plant grow light LED chip 12 and an ultraviolet LED chip 13; the multifunctional light source assembly is controlled to perform one or more functions of illumination, plant growth assistance and sterilization. As shown in FIG. 1, the illumination LED chip 11 is provided in the area between the dotted circle A and the dotted circle B, the plant grow light LED chip 12 is provided in the area between the dotted circle B and the dotted circle C, and the ultraviolet LED chip 13 is provided in the area inside the dotted circle C.

Specifically, the illumination LED chip 11 is configured to emit light for illumination, such as white light; the white light is a composite light, and is generally a mix of two colors of light or three colors of light, when the white light passes through a prism, since the refractive indexes of light of different wavelengths are different, the white light is divided into a variety of colors, when any two of the three primary colors are overlapped with each other, a secondary color will be generated, and three primary colors are mixed with each other to obtain the color white. The plant grow light LED chip 12 is configured to emit full-spectrum light and its waveband preferably includes a blue light waveband of 400-499 nm and a red light waveband of 600-699 nm, which are favorable to plant growth. The ultraviolet LED chip 13 is configured to emit ultraviolet light, and its preferred waveband is 315-400 nm.

It should be noted that, in the multifunctional light-emitting device of the present disclosure, one function can be used at a time, such as the illumination function for reading and writing, the sterilization function for eliminating bacteria, or the plant growth assistance function for cultivating plants. During actual applications, two functions can be used at the same time; for example, while the ultraviolet light is turned on for sterilization, the illumination light can also be turned on to serve as an indicating light, thereby enhancing the safety of the lamp. In some cases, the three types of light can also be turned on at the same time to enable the functions of illumination, sterilization, and plant growth assistance at the same time.

In some examples, the multifunctional light-emitting device further includes a control part, and the control part correspondingly controls the light source assembly when responding to a user operation, such that the light source assembly performs one or more functions of illumination, plant growth assistance, and sterilization. For example, the control part may be a physical switch or a touch switch; the user can control the light-emitting device through the control part, to control the light-emitting device to emit the light for illumination, the plant grow light, or the ultraviolet light.

It should be noted that the control part includes a micro-controller, such as an MCU micro-controller, an SoC micro-controller, an SCM micro-controller, etc., where the functions of a central processing unit (CPU) with data processing capability, a random access memory (RAM), a read only memory (ROM), multiple I/O ports and an interrupt system, a timer/counter, etc. (and possibly including display driver circuits, pulse width modulation circuits, analog multiplexers, A/D converters, etc.) are integrated on a silicon chip through an ultra-large-scale integrated circuit technology.

Figure 2:
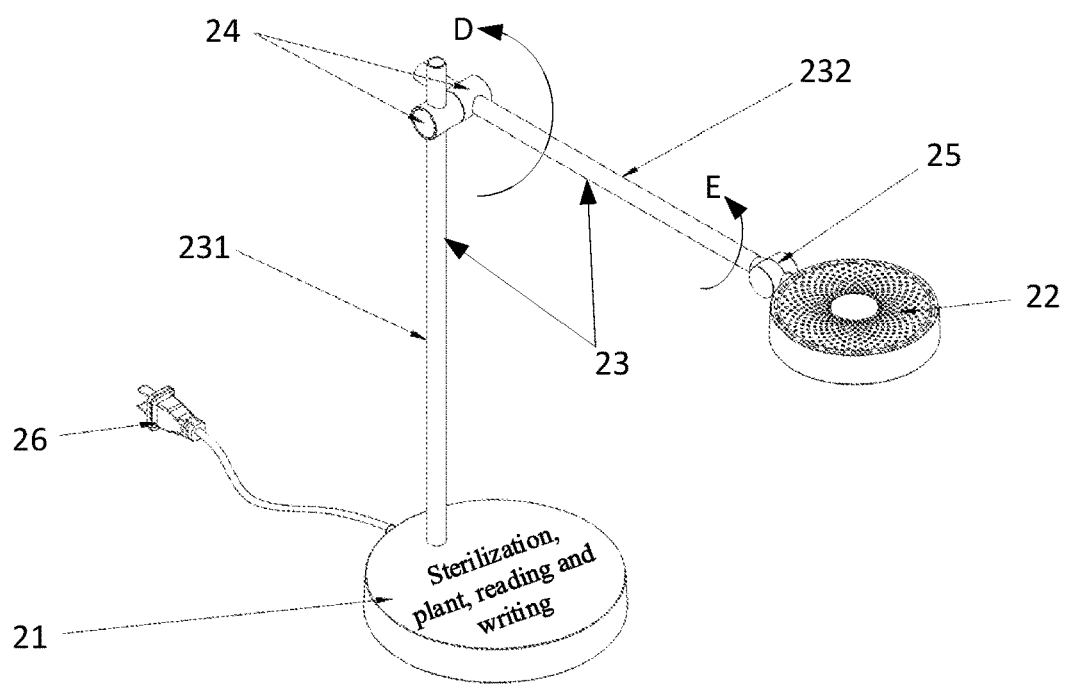
FIG. 2 shows a structural diagram of a multifunctional desk lamp according to an embodiment of the present disclosure.

In some examples, the multifunctional light-emitting device further includes a communication part, and the communication part establishes a communication connection with an external control device, to correspondingly control the light source assembly to perform one or more functions of illumination, plant growth assistance and sterilization after receiving light control instructions from the external device. In the present example, the external control device may be a cell phone (i.e., the user controls the light-emitting device via a cell phone app) or a control part independent of the light-emitting device (e.g., a remote control, etc.). It should be noted that the communication part may be a Bluetooth communication module, a Wi-Fi communication module, an NB-IoT communication module, a ZigBee communication module, or a LoRa communication module, As shown in FIG. 2, the present disclosure provides a multifunctional desk lamp. The multifunctional desk lamp of the present embodiment includes a base assembly 21, a lamp head assembly 22 and a lamp arm assembly 23, wherein one end of the lamp arm assembly 23 is connected with the base assembly 21, and the other end is connected with and supports the lamp head assembly 22.

In some examples, the lamp arm assembly 23 includes a vertical arm 231 and a horizontal arm 232; a first end of the vertical arm 231 is connected with the base assembly 21, a second end of the vertical arm 231 is connected with a first end of the horizontal arm 232 through a first rotating part 24, and a second end of the horizontal arm 232 is connected with the lamp head assembly 22 through a second rotating part 25. The first rotating part 24 rotates and drives the horizontal arm 232 and the lamp head assembly 22 to rotate around the vertical arm 231; and the second rotating part 25 rotates and drives the lamp head assembly 22 to rotate around the horizontal arm 232.

For example, the first rotating part 24 may rotate in the direction represented by a curved arrow D as shown in FIG. 2, to drive the horizontal arm 232 to rise upwards, so as to drive the lamp head assembly 22 to rise upwards too (i.e., increasing the height of the lamp head assembly 22); the first rotating part 24 may also rotate in the opposite direction of D to lower the horizontal arm 232, so as to lower the lamp head assembly 22 as well (i.e., decreasing the height of the lamp head assembly 22). For another example, the second rotating part 25 can rotate in the direction represented by a curved arrow E and drive the lamp head assembly 22 to tilt upwards, i.e., increasing the elevation angle of the lamp head assembly 22; the second rotating part 25 can also rotate in the opposite direction of E so as to drive the lamp head assembly 22 to tilt downwards, i.e., reducing the elevation angle of the lamp head assembly 22. In the present embodiment, through the cooperation of the horizontal arm 232, the vertical arm 231 and the rotating parts 24, 25, the height and angle of the lamp head assembly 22 can be adjusted as needed.

Further, the rotating parts can be universal joints, so the first rotating part 24 can rotate to drive the horizontal arm 232 and the lamp head assembly 22 to rotate around the vertical arm 231 along any angle, for example, the horizontal arm 232 and the lamp head assembly 22 can be adjusted upwards, downwards, leftwards, rightwards, to the upper left, to the lower left, to the upper right, to the lower right, etc.; similarly, the second rotating part 25 can drive the lamp head assembly to rotate around the horizontal arm 232 along any angle.

In some examples, the base assembly 21 includes a drive power module and a touch panel; when the touch panel is touched, it transmits corresponding lamp control instructions to the drive power module through an interface; the drive power module is configured to have three light control circuits, and each light control circuit is configured to independently drive different LED chips. For example, in a sterilization scenario, if the user touches, for example, a word "sterilization" on the touch panel, the drive power module will drive a ultraviolet LED chip to emit ultraviolet light; in a plant growth assistance scenario, if the user touches, for example, a word "plant" on the touch panel, the drive power module will drive a plant grow light LED chip to emit plant grow light; in the reading and writing scenario, if the user touches, for example, words "read/write" on the touch panel, the drive power module will drive an illumination LED chip to emit light for illumination, for example, white light.

In some examples, the multifunctional desk lamp further includes an electrical connecting part 26, such as an electrical plug through which the desk lamp obtains electricity, and a switch or switches connected in series may be disposed between the electrical connecting part 26 and the other parts of the desk lamp as needed, so that it is convenient for the user to turn off or turn on the desk lamp.

Figure 3:
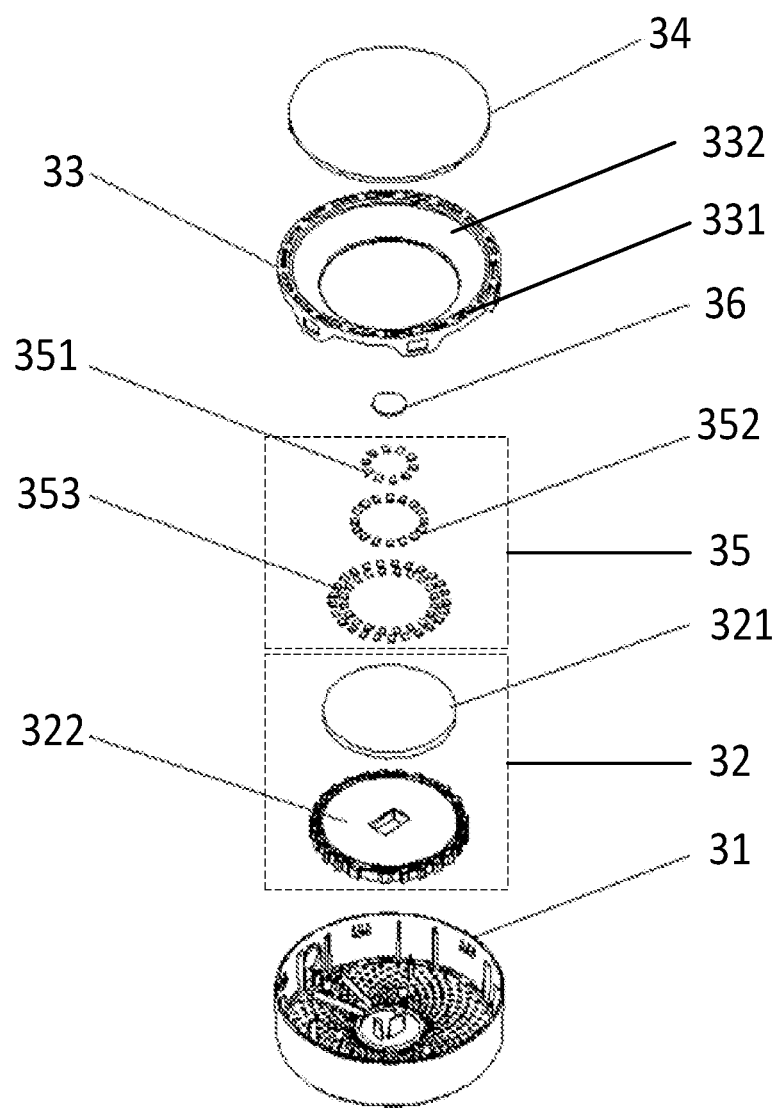
FIG. 3 shows a structural diagram of a lamp head assembly according to an embodiment of the present disclosure.

The structure of the lamp head assembly 22 in an example is as shown in FIG. 3, which includes a lamp cover 31, a heat dissipation part 32, a cover plate 33, and a lens 34, wherein the lamp cover 31 includes an accommodating space for accommodating the lamp head assembly 22, the heat dissipation part 32 is arranged in the accommodating space of the lamp cover 31, the cover plate 33 covers the lamp cover 31, and the lens 34 is arranged on the cover plate 33.

Specifically speaking, the heat dissipation part 32 includes a ceramic radiator 321 and an aluminum radiator 322; one side of the ceramic radiator 321 is for attaching to the light source assembly 35 and the other side thereof is connected with the aluminum radiator 322. In one embodiment, the ceramic radiator 321 and the aluminum radiator 322 are connected by glue. Adopting both the ceramic radiator and the aluminum radiator leads to a good heat dissipation, insulation and corrosion resistance. Since the ceramic material is used, there is no need to re-applying acrylic oligomers coatings for insulation.

Further, the cover plate 33 and the lamp cover 31 are connected by buckles, and therefore, when in use, the cover plate 33 is pressed against the ceramic radiator 321, and the lens 34 and the cover plate 31 are also connected by buckles. Adopting the buckles saves the cost of screws and other related materials, therefore avoids the process of locking screws and other related processes, and facilitates assembly and production.

The light source assembly 35 includes an ultraviolet LED chip 351, a plant grow light LED chip 352 and an illumination LED chip 353. The illumination LED chip 353 is configured to emit light for illumination, such as white light; the white light is a composite light, and is usually a mix of two colors of light or three colors of light, when the white light passes through a prism, since the refractive indexes of light of different wavelengths are different, the white light is divided into a variety of colors, when any two of the three primary colors are overlapped with each other, a secondary color will be generated, and three primary colors are mixed with each other to obtain the color white. The plant grow light LED chip 12 is configured to emit full-spectrum light and its waveband preferably includes a blue light waveband of 400-499 nm, and a red light waveband of 600-699 nm, which are favorable to plant growth. The ultraviolet LED chip 13 is configured to emit ultraviolet light, and its preferred waveband is 315-400 nm.

In some examples, the light source assembly 35 may be attached to a surface of the ceramic radiator 321 by means of mounting, or the LED chip may be packaged by chip-on-board (COB) packaging. It should be understood that, COB packaging is a packaging technology in which a bare chip is adhered to an interconnected substrate with a conductive or non-conductive adhesive and then the bare chip is subjected to wire bonding to achieve electrical connection, thereby avoiding direct exposure of the chip to the air and avoiding contamination or artificial damages that may destroy the chip's ability to function normally.

In some examples, the cover plate 33 includes three light-transmitting areas respectively corresponding to the illumination LED chip, the plant grow light LED chip and the ultraviolet LED chip, to realize different applications. Specifically speaking, the lens 34 arranged on the cover plate is a Fresnel lens; the three light-transmitting areas of the cover plate include a hollow part 331 for transmission of the ultraviolet light, a bright surface lens 332 for transmission of the plant grow light, and the Fresnel lens 34 for transmission of the light for illumination.

Preferably, the light for illumination emitted by the illumination LED chip radiates outwards through the Fresnel lens, and the Fresnel lens shatters the rays of light originally emitted so that the shattered rays cover a desktop lighting range of the desk lamp with improved light intensity uniformity in the center and edges of the desktop lighting range. The plant grow light emitted by the plant grow light LED chip radiates outwards through the bright surface lens; the ultraviolet LED chip irradiates outwards directly through the hollow part on the cover plate 33 and does not irradiates through the lens; such arrangement increases the efficiency of the ultraviolet LED chip, and results in a better sterilization effect, while prevents the lens from being yellowed due to direct radiation by the ultraviolet light.

In some examples, the desk lamp further includes a power adapter board 36 for adapting to power supplies, such as converting an AC supply (such as commercial power supply) to a DC low-voltage power supply (e.g., 5V, 3V, etc.) required to drive the LEDs.

In summary, the present disclosure provides a multifunctional light source assembly and a multifunctional desk lamp applying the same; the desk lamp head of the present disclosure is provided with an illumination chip, a plant grow light chip and an ultraviolet chip which are respectively connected to the controller, which respectively control the three chips through the on and off of currents so that functions such as illumination for reading and writing, ultraviolet sterilization, and plant growth assistance can be achieved. In addition, while the ultraviolet light is turned on for sterilization, the illumination light can also be turned on to serve as an indicating light, thereby enhancing the safety of the lamp; compared to traditional methods for heat dissipation, the heat dissipation method herein that adopts both aluminum and ceramic materials is more efficient, and has a better insulation effect and corrosion-resistance property, thereby improving the overall performance of the lamp. Therefore, the present disclosure effectively overcomes various shortcomings of the prior art and has a high industrial value.

The above embodiments are merely illustrative of the principles of the present disclosure and the effects, and are not intended to limit the present disclosure. Those skilled in the art may modify or change the above embodiments without violating the spirit and scope of the present disclosure. Therefore, all the equivalent modifications or changes made by those with ordinary knowledge in the art without departing from the spirit and technical ideas revealed by the present disclosure shall all fall within the scope covered by the claims of the present disclosure.

What is claimed is:

1. A multifunctional desk lamp, comprising:
    a base assembly;
    a lamp head assembly; and
    a lamp arm assembly, wherein one end of the lamp arm assembly is connected with the base assembly, and the other end of the lamp arm assembly is connected with and supports the lamp head assembly;
    wherein the lamp head assembly is internally provided with a multifunctional light source assembly, the multifunctional light source assembly comprises an illumination LED chip, a plant grow light LED chip and an ultraviolet LED chip; and the light source assembly is controlled to perform one or more functions of illumination, plant growth assistance, and sterilization;
    wherein the lamp head assembly comprises:
        a lamp cover, comprising an accommodating space;
        a heat dissipation part, arranged in the accommodating space for accommodating the light source assembly;
        a cover plate, covering the lamp cover; and
        a lens, arranged on the cover plate;
        wherein the cover plate comprises three light-transmitting areas corresponding to the illumination LED chip, the plant grow light LED chip, and the ultraviolet LED chip, respectively;
        wherein the lens arranged on the cover plate is a Fresnel lens; the three light-transmitting areas of the cover plate comprise a hollow part for transmission of ultraviolet light, a surface lens for transmission of plant grow light, and the Fresnel lens for transmission of light for illumination.

2. The multifunctional desk lamp of claim 1, wherein the lamp arm assembly comprises:
    a vertical arm, wherein a first end of the vertical arm is connected with the base assembly;
    a horizontal arm, wherein a first end of the horizontal arm is connected with a second end of the vertical arm through a first rotating part, and a second end of the horizontal arm is connected with the lamp head assembly through a second rotating part;
    wherein the first rotating part rotates and drives the horizontal arm and the lamp head assembly to rotate around the vertical arm; and the second rotating part rotates and drives the lamp head assembly to rotate around the horizontal arm.

3. The multifunctional desk lamp of claim 1, wherein the heat dissipation part comprises a ceramic radiator and an aluminum radiator; one side of the ceramic radiator is for attaching to the light source assembly and the other side of the ceramic radiator is connected with the aluminum radiator.

4. The multifunctional desk lamp of claim 1, wherein the base assembly comprises a drive power module and a touch panel; when the touch panel is touched, it transmits corresponding lamp control instructions to the drive power module through an interface; the drive power module is configured with three light control circuits, and each of the light control circuits is configured to independently drive one of the LED chips.

* * * * *